(12) United States Patent
Haik

(10) Patent No.: US 7,527,979 B2
(45) Date of Patent: May 5, 2009

(54) DEVICES AND METHODS FOR RAPID DETECTION OF PATHOGENS

(75) Inventor: Yousef Haik, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 508 days.

(21) Appl. No.: 11/204,459

(22) Filed: Aug. 16, 2005

(65) Prior Publication Data

US 2006/0211061 A1 Sep. 21, 2006

Related U.S. Application Data

(60) Provisional application No. 60/602,417, filed on Aug. 18, 2004.

(51) Int. Cl.
*G01N 33/553* (2006.01)
*G01N 33/53* (2006.01)

(52) U.S. Cl. .................. 436/526; 436/518; 435/7.5; 435/7.94; 435/34; 435/39; 435/4; 435/7.37

(58) Field of Classification Search ................ 436/526, 436/518; 435/7.5, 7.72, 7.94, 34, 39, 5, 7.37
See application file for complete search history.

(56) References Cited

U.S. PATENT DOCUMENTS

| | | | |
|---|---|---|---|
| 6,132,607 A | 10/2000 | Chen et al. | |
| 2004/0065969 A1 | 4/2004 | Chatterjee et al. | |
| 2004/0146529 A1 | 7/2004 | Chen et al. | |

OTHER PUBLICATIONS

Abdel-Hamid, et al., "Flow-through immunofiltration assay system for rapid detection of *E. coli 0157:H7*," Biosensors & Bioelectronics, 14:309-16 (1999).
Achar, et al., "Diagnosis of acute coronary syndrome," American Family Physician, 72(1):119-126 (2005).
Adams, et al., "Biochemical markers of myocardial injury. Is MB creatine kinase the choice for the 1990s?," Circulation, 88(2):750-763 (1993).
Adams, "Clinical application of markers of cardiac injury: basic concepts and new considerations," Clinica Chimica Acta, 284:127-134 (1999).

(Continued)

*Primary Examiner*—Christopher L Chin
*Assistant Examiner*—Pensee T Do
(74) *Attorney, Agent, or Firm*—Sutherland Asbill & Brennan LLP

(57) ABSTRACT

Assay systems and methods are provided for detecting a target pathogen, such as a microorganism (e.g., bacterium, bacterial toxin) which may be present in a fluid or other location. The method can include linking a magnetic microparticle to a first epitope of the target microorganism in a fluid via a first antibody; utilizing a magnetic field to separate the magnetic microparticle and linked targeted microorganism from at least a portion of other components in the fluid, thereby forming a test sample; linking a glucose molecule to a second epitope of the target microorganism via a second antibody; and detecting the glucose in the test sample to determine the presence or concentration of the target microorganism in the fluid. The glucose detection preferably is one that can be done rapidly, e.g., with a conventional glucometer, and may include measuring the electrical resistance, color, or pH of the test sample.

20 Claims, 2 Drawing Sheets

ï  Glucose molecule

♦  Biotinylated Con-A Lectin

◎  Streptavidin

Y  Biotinylated Anti-*E.coli* Endotoxin Antibody

■  E.coli strain [BL21 Star (DE3)pLysS]

Y  Biotinylated Anti-*E.coli* Rabbit Antibody

●  Para-Magnetic Microsphere

OTHER PUBLICATIONS

Bayliss, "*MAFF Research Program FS 12, Detection and Separation of Pathogens and their Toxins*," MAFF UK, Center for Applied Microbiology and Research, Porton Down (1999).

Berroeta, et al., "*The use of cardiac troponins ( T or I) measurement in cardiology and various clinical setting*," Ann Fr Anesth Reanim, (2005).

Chatterjee, et al., "*Size dependent magnetic properties of iron oxide nanoparticles*," Journal of Magnetism and Magnetic Materials, 257:113-118 (2003).

Chen, et al., "*Role of heart-type fatty acid binding protein in early detection of acute myocardial infarction in comparison with cTnI, CK-MW and myoglobin*," Journal of Huazhong University of Science and Technology [Med Sci], 24(5):449-51, 459 (2004).

Cole, et al., "*The EBV-hybridoma technique and its application to human lung cancer*," Monoclonal Antibodies and Cancer Therapy, pp. 77-96 (1985).

Cubrilo-Turek, et al., "*New biochemical markers in the assessment of minor myocardial damage in critically ill patients*," Acta Med Croatica, 58(5):381-8 (2004).

De Winter, et al., "*Value of myoglobin, troponin T, and CK-MB$_{mass}$ in ruling out an acute myocardial infarction in the emergency room*," Circulation, 92:3401-3407 (1995).

Eggers, et al., "*Combining different biochemical markers of myocardial ischemia does not improve risk stratification in chest pain patients compared to troponin I alone*," Coronary Artery Disease, 16(5):315-19 (2005).

Eggers, et al., "*Diagnostic value of serial measurement of cardiac markers in patients with chest pain: limited value of adding myoglobin to troponin I for exclusion of myocardial infarction*," American Heart Journal, 148(4):574-581 (2004).

Eisenman, et al., "*Are all troponin assays equivalent in the emergency department?*," Singapore Med. J., 46(7):325-327 (2005).

Feldsine, et al., "*Visual immunoprecipitate Assay (VIP) for detection of enterohemorrhagic Escherichia coli (EHEC) O157:H7 in selected foods: collaborative study*," Journal of AOAC International, 80(3):517-29 (1997).

Galfre, et al.., "*Antibodies to major histocompatibility antigens produced by hybrid cell lines*," Nature, 266:550-52 (1977).

Galvani, et al., "*New markers for early diagnosis of acute myocardial infarction*," International Journal of Cardiology, 65(Suppl. 1):S17-S22 (1998).

Gefter, et al., "*A simple method for polyethylene glycol-promoted hybridization of mouse myeloma cells*," Somatic Cell Genet., 3:231-36 (1977).

Gibler, et al., "*Early detection of acute myocardial infarction in patients presenting with chest pain and nondiagnostic ECGs: Serial CK-MB sampling in the emergency department*," Annals of Emergency Medicine, 19:1359-66 (1990).

Haik, et al., "*Development of magnetic device for cell separation*," Journal of Magnetism and Magnetic Materials, 194:254-61 (1999).

Héden, et al., "*Acute myocardial infarction detected in the 12-lead ECG by artificial neural networks*," Circulation, 96:1798-1802 (1997).

Hedges, et al, "*Serial ECGs are less accurate than serial CK-MB results for emergency department diagnosis of myocardial infarction*," Annals of Emergency Medicine, 21(12):1445-50 (1992).

Hudson, et al., "*Cardiac markers: point of care testing*," Clinica Chimica Acta, 284:223-237 (1999).

Ishii, et al., "*Prognostic value of serum concentration of heart-type fatty acid-binding protein relative to cardiac troponin T on admission in the early hours of acute coronary syndrome*," Clinincal Chemistry, 51(8):1397-1404 (2005).

Johnson, et al., "*Comparison of the BAX for screening/E.coli 0157:H7 method with conventional methods for detection of extremely low levels of Escherichia coli 0157:H7 in ground beef*," Applied and Environmental Microbiology, 64(11):4390-95 (1998).

Kennett, et al., "*Monoclonal antibodies: a new dimension in biological analyses*," Plenum Press: New York and London (1980).

Kim, et al., "*Use of chicken egg-yolk antibodies against K88+fimbrial antigen for quantitative analysis of enterotoxigenic Escherichia coli (ETEC) K88+ by a sandwich ELISA*," Journal of the Science of Food and Agriculture, 79:1513-18 (1999).

Kohler, et al., "*Continuous cultures of fused cells secreting antibody of predefined specificity*," Nature, 256:495-97 (1975).

Kozbor, et al., "*The production of monoclonal antibodies from human lymphocytes*," Immunology Today, 4(3):72-79 (1983).

Lerner, "*How to make a hybridoma*," The Yale Journal of Biology and Medicine, 54:387-402 (1981).

Lin, et al., "*Rates of positive cardiac troponin I and creatine kinase MB mass among patients hospitalized for suspected acute coronary syndromes*," Clinical Chemistry, 50(2):333-38 (2004).

McCarthy, et al., "*Missed diagnosis of acute myocardial infarction in the emergency department: Results from a multicenter study*," Annals of Emergency Medicine, 22(3):579-82 (1993).

Ogunjimi, et al., "*Adsorption of endogenous polyphenols relieves the inhibition by fruit juices and fresh produce of immuno-PCR detection of Escherichia coli 0157:H7*," FEMS Immunology and Medical Microbiology, 23:213-20 (1991).

Padhye, et al., "*Production and characterization of a monoclonal antibody specific for enterohemorrhagic Escherichia coli of serotypes O157:H7 and O26:H11*," Journal of Clinical Microbiology, 29(1):99-103 (1991).

Panteghini, "*Diagnostic application of CK-MB mass determination*," Clinica Chimica Acta, 272:23-31 (1998).

Penttila, et al., "*Myoglobin, creatine kinase MB isoforms and creatine kinase MB mass in early diagnosis of myocardial infarction in patients with acute chest pain*," Clinical Biochemistry, 35:647-53 (2002).

Puleo, et al., "*Use of rapid assay of subforms of creatine kinase MB to diagnose or rule out acute myocardial infarction*," New England Journal of Medicine, 331(9): 561-66 (1994).

Roberts, et al., "*Earlier diagnosis and treatment of acute myocardial infarction necessitates the need for a 'new diagnostic mind-set'*," Circulation, 89(2):872-881 (1994).

Sallach, et al., "*A change in serum myoglobin to detect acute myocardial infarction in patients with normal troponin I levels*," American Journal of Cardiology, 94:864-867 (2004).

Shelton, et al., "*Evaluation of parameters affecting quantitative detection of Escherichia coli 0157 in enriched water samples using immunomagnetic electrochemiluminescence*," Journal of Microbiological Methods, 55:717-25 (2003).

Suter, et al., "*The immunochemistry of sandwich elisas—III. The stoichiometry and efficacy of the protein-avidin-biotin capture (PABC) system*," Molecular Immunology, 26(3):221-30 (1989).

Van Nieuwenhoven, et al., "*Discrimination between myocardial and skeletal muscle injury by assessment of the plasma ratio of myoglobin over fatty acid-binding protein*," Circulation, 92:2848-54 (1995).

Vote, et al., "*Blood glucose meter performance under hyperbaric oxygen conditions*," Clinica Chimica Acta, 305:81-87 (2001).

Wodzig, et al., "*Estimation of myocardial infarct size from plasma myoglobin or fatty acid-binding protein. Influence of renal function*," European Journal of Clinical Chemistry and Clinical Biochemistry, 35(3):191-98 (1997).

Wright, et al., "*Immunomagnetic separation as a sensitive method for isolating Escherichia coli O157 from food samples*," Epidemiology and Infection, 113:31-39 (1994).

Yu, et al., "*Development of a magnetic microplate chemifluorimmunoassay for rapid detection of bacteria and toxin in blood*," Analytical Biochemistry, 261:1-7 (1998).

Yu, et al., "*Immunomagnetic-electrochemiluminescent detection of Escherichia coli O157 and salmonella typhimurium in foods and environmental water samples*," Applied and Environmental Microbiology, 62(2):587-92 (1996).

DEVICES AND METHODS FOR RAPID DETECTION OF PATHOGENS

CROSS-REFERENCE TO RELATED APPLICATIONS

This application claims the benefit of U.S. Provisional Application No. 60/602,417, filed Aug. 18, 2004. The application is incorporated herein by reference in its entirety.

BACKGROUND OF THE INVENTION

This invention relates generally to immunoassays for microbial detection, and more particularly to methods for rapidly detecting pathogenic microbes.

Rapid detection of biological agents used as warfare agents, terrorist threat agents, and emerging diseases are significant military and civilian challenges. For instance, biological agents when effectively prepared are extremely potent and could be disseminated to incapacitate or kill thousands of persons. It has been reported that during the Gulf War, U.S. and allied forces suffered from a lack of reliable biological agent detection systems. While a number of detection systems were developed to overcome this problem, several of these methods fail to reliably provide the accuracy, sensitivity, and speed desired. In addition, worldwide 22 million people die annually of infectious diseases. Bacterial infections are responsible for a high percentage of these fatal infections. Accordingly, there is a need for methods that can quantitatively and sensitively detect bacterial pathogens for multiple medical and industrial purposes, including biological warfare defenses.

A bacterial detection method should be reliable. That is, it should measure relatively the exact number of the pathogen multiple times under the same conditions. Moreover, speed is critical to the acceptability of the detection method.

Traditionally, detection of microorganisms relies on the same biochemical basis developed by Pasteur and others in the last century and the disk diffusion method developed by Kirby-Bauer for antimicrobial susceptibility testing (e.g., Wright, et al., *Epidemiol. Infec.* 113:31-39 (1994)). During the last decade, emphasis had been on automation of these basic biochemical tests. This has accelerated the identification process, but even with the most sophisticated system, the process still takes at least roughly thirty hours under optimal conditions for a precise diagnosis of bacterial infection.

An example of a bacterial pathogen is *Escherichia coli* BL21 Star (DE3) pLysS, which is a specific strain of *E. coli* that can potentially causes moderate to severe diseases for organism's eyes, skin, lung and digestive tract (Invitrogen Corporation, MSDS for BL21 Star™ (DE3) One Shot™ Chemically Competent *E. coli*.). Clinical symptoms include eye tearing, reddening, and temporary vision impairment (cloudy or blurred vision); skin irritation, defatting, and dermatitis; dizziness, weakness, fatigue, nausea, and headache if inhaled; abdominal discomfort, nausea, vomiting and diarrhea if ingested. Magnetic immunoassay for isolation *E. coli* was reported by Wright et al., *Epidemiol. Infec.* 113:31-39 (1994) with an assay time of approximately 24 hrs. Detection methods for *E. coli* based on enzyme-linked immunosorbent assays (ELISA) (Padhye & Doyle, *J. Clin. Microbiol.* 29:99-103 (1991)) and polymerase chain reaction (PCR) (Johnson, et al., *Appl. Environ. Microbiol.* 64:4390-95 (1998)) have been developed and improvements in their performance time and sensitivity are ongoing. PCR detection methods have the possibility of single cell detection with the potential of taking less than eight hours to perform (Ogunjimi & Choudray, *FEMS Immunol. Med. Microbiol.* 23:213-20 (1991)). However, some molecular methods of bacterial detection have not been fully accepted by routine microbiology testing laboratories. This may be due to the need for relatively expensive equipment and associated specialist skills to perform the analyses (Bayliss, *MAFF Research Program FS* 12, *Detection and Separation of Pathogens and their Toxins*. MAFF UK, Center for Applied Microbiology and Research, Porton Down (1999)). By comparison, immunological detection tests for bacterial pathogens (including latex agglutination, immunomagnetic separation, lateral flow immunoassays and ELISA) are used frequently. Furthermore, ELISA detection methods have sensitivities of $10^5$-$10^7$ bacterial cells/ml$^{-1}$ (Kim, et al., *J. Sci. Food Agric.* 79:1512-18 (1999)) and require overnight enrichment of the sample prior to analysis (Feldsine, *Food Biol. Contam.* 80:517-29 (1997)). Some sensitive immunological methods have been developed using electro-chemiluminescence (Yu & Bruno, *Appl. Environ. Microbiol.* 62:587-92 (1996) and rapid flow through systems (Abdelhamid et al., *Biosensors Bioelect.* 14:309-16 (1999)). Current detection methods have led to the possibility of detection within a single working day.

Hand held devices for rapid detection of pathogens have been proposed to be used by emergency medical services, fire and rescue services, hazmat teams, and other first responders. However, pathogen detection kits currently available are not accurate for on-the-scene decision-making and require significant user training.

In addition, the possibility of relatively low concentrations of collectable bacteria at a particular site of investigation/testing would be expected to challenge or refute detection by traditional culture methods. For instance, studies suggest that only 1-10% of ambient bacteria are culturable (Padhye & Doyle, *J. Clin. Microbiol.* 29:99-103 (1991)). According to the Center for Biological Defense, aerosolized bacteria are of major concern when used for warfare or terrorist attack. It would therefore be desirable to provide a portable, lightweight, and easy-to-use device for pathogen detection. It would also be desirable to provide means for rapidly detecting pathogens with high sensitivity.

SUMMARY OF THE INVENTION

Assay systems and methods are provided for detecting an target pathogen. In one aspect, the method is for detecting (e.g., presence and/or concentration of) a target microorganism in a fluid. In one embodiment, the method includes linking a magnetic microparticle to a first epitope of the target microorganism in a fluid via a first antibody; utilizing a magnetic field to separate the magnetic microparticle and linked targeted microorganism from at least a portion of other components in the fluid, thereby forming a test sample; linking a glucose molecule to a second epitope of the target microorganism via a second antibody; and detecting the glucose in the test sample to determine the presence or concentration of the target microorganism in the fluid. In one embodiment, the target microorganism comprises a bacterium or bacterial toxin, e.g., an *E. Coli*. In another embodiment, the target microorganism is a virus.

In one embodiment, the magnetic microparticles comprise microspheres coated with a polymer or protein. For example, the coating can include albumin, avidin, or a combination thereof.

In various embodiments, the glucose detection comprises measuring the electrical resistance, color, or pH of the test sample. For example, the glucose detection may comprise measuring light transmittance through the test sample. Alternatively, the glucose detection may comprises oxidation of the glucose to gluconic acid at a platinum electrode, as would be utilized with certain conventional glucometers.

In one embodiment, the first antibody comprises a biotinylated anti-*E. coli* rabbit antibody. The second antibody can comprise an anti-*E. coli* endotoxin antibody. In a particular embodiment, the second antibody is linked to streptavidin, which is linked to a lectin, which is linked to the glucose molecule.

In one specific embodiment, the method for detecting a target bacterium in a fluid includes the following steps: combining the fluid with magnetic microparticles linked to a first antibody, said first antibody binding to a first site on the target bacterium, if any, present in the fluid; applying a magnetic field to the fluid effective to separate the linked magnetic microparticles and target bacterium from the fluid, forming a test sample; combining the test sample with a second antibody, said second antibody binding to a second site on the target bacterium, wherein said second antibody is linked to a glucose molecule; and detecting the glucose in the test sample to determine the presence or concentration of the target bacterium in the fluid sample. In one embodiment, the microparticles are microspheres which comprise a core of a superparamagnetic material coated with a protein or polymer.

In one specific example, the first biotinylated antibody can include a biotinylated anti-*E. coli* Rabbit antibody, and the second biotinylated antibody can be linked to streptavidin, which in turn can be linked to a biotinylated lectin, linked to the glucose molecule. For instance, the biotinylated lectin can be a Con-A lectin and the second biotinylated antibody comprises anti-*E. coli* endotoxin antibody.

In another aspect, an immunoassay system is provided, which includes a first antibody linkable to an assayable target pathogenic antigen; a magnetic microparticle linked to the first antibody; a second antibody linkable to the assayable target pathogenic antigen; and a glucose molecule linked to the second antibody. In still another aspect, an immunoassay kit is provided for detecting a target pathogen. For example, it may include a first part which comprises magnetic microparticles linked to antibodies selected to be linkable to a first epitope of the target pathogen; and a second part which comprises second antibodies selected to be linkable to a second epitope of the target pathogen, wherein the second antibody is linked to a lectin that is linked or linkable to a glucose molecule or enzyme tag.

DETAILED DESCRIPTION OF THE PREFERRED EMBODIMENT

Improved assays and methods have been developed using magnetic immunoassay technology to separate the target of interest from a fluid sample and detect minute concentrations of an assayable target antigen, in particular pathogenic microorganisms.

Figure 1:
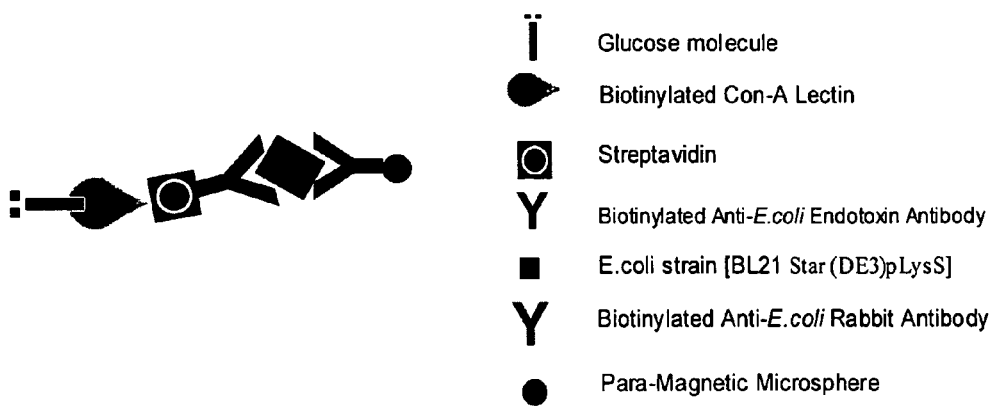
FIG. 1 is a schematic representation of one embodiment of the magnetic immunoassay described herein for detection of *Escherichia coli*.

In a preferred embodiment, the assay utilizes a magnetic solid-phase enzyme linked immunoassay (magnetic ELISA), wherein the sandwich forms by attaching two different antibodies to different epitopes on pathogenic microorganisms (e.g., a bacterium). One antibody is attached to a solid surface of the magnetic microsphere, and the other is attached to a glucose molecule. The first antibody is used for the separation of the pathogenic microorganisms from an environmental sample whereas, the second antibody, attached to some glucose molecules, is used to detect the presence or concentration of the pathogenic microorganisms in the sample. FIG. 1 shows a schematic representation of one embodiment of the magnetic immunoassay. In a preferred embodiment, the pathogen is bound to glucose and the glucose concentration is measured using or adapting conventional approaches for glucose measurement. The immunoassay can be incorporated into a kit and/or device for portable use, for example by first responders, military, or healthcare workers.

The present immunoassay provides a platform adaptable for detecting essentially any molecule that has an epitope specific antibody. The technique preferably includes (a) magnetic separation using a direct and specific link with the molecule, such as an antibody-antigen coupling or a site-specific coupling (e.g., glucoproteins on red blood cells), and (b) detection using a label detectable by a glucometer. One need only identify two suitable epitopes on the molecule: one for linking the magnetic particle, and one for linking the glucose molecule (or other enzymatic label). In a preferred embodiment, a magnetic sandwich immunoassay provides for rapid isolation and detection of a targeted pathogen.

As used herein, the term "antibody" is intended to include immunoglobulin molecules and immunologically active portions of immunoglobulin molecules, i.e., molecules that contain an antigen-binding site that specifically binds (immunoreacts with) an antigen, such as Fab and $F(ab')_2$ fragments. As used herein, the term "antibody" includes polyclonal and monoclonal antibodies, and variants such as single-chain (recombinant) antibodies, "humanized" chimeric antibodies, and immunologically active fragments of antibodies. For the purposes of this invention, a "chimeric" monoclonal antibody is a murine monoclonal antibody comprising constant region fragments (Fc) from a different animal. For the purposes of this invention, a "humanized" monoclonal antibody is a murine monoclonal antibody in which human protein sequences have been substituted for all the murine protein sequences except for the murine complementarity determining regions (CDR) of both the light and heavy chains. Standard techniques for the generation and isolation of antibodies are well known and commonly employed by those of skill in the art. A number of standard techniques are described in Kohler & Milstein, *Nature* 256:495-97 (1975); Kozbor et al., *Immunol Today* 4:72 (1983); Cole et al., Monoclonal Antibodies and Cancer Therapy, pp. 77-96 (Alan R. Liss, Inc., 1985); Kenneth, in Monoclonal Antibodies: A New Dimension In Biological Analyses (Plenum Publishing Corp., New York, N.Y. 1980); Lemer, *Yale J. Biol. Med.*, 54:387-402 (1981); Gefter et al., *Somatic Cell Genet.*, 3:231-36 (1977); and Galfre et al., *Nature* 266:55052 (1977).

Complementary clones of an antibody are useful in the detection of the assayable antigen. As used herein, "complementary clones" of an antibody means antibodies that bind non-overlapping epitopes on the same antigen.

As used herein, the terms "comprise," "comprising," "include," and "including" are intended to be open, non-limiting terms, unless the contrary is expressly indicated.

Rapid Detection Method and Assay

In one aspect, a method is provided for detecting a microorganism that may or may not be present in a fluid. Essentially any fluid can be tested that does not include components that would interfere with or undesirably react with the components of the immunoassay. In various embodiments, the fluid is taken from blood or another mammalian physiological fluid, or from the environment (e.g., air sample, water, sample, soil sample, surfaces and air in buildings, etc.).

In one embodiment, the assay method includes the steps of linking (via a first antibody) a magnetic particle to one epitope of the microorganism, if any, present in a bulk fluid; linking (via a second antibody) a glucose molecule to another epitope of the microorganism; utilizing a magnetic field to separate the magnetic particle and linked microorganism from the bulk fluid, thereby forming a test fluid; and measuring the concentration of glucose molecules in the test fluid to determine the presence and/or concentration of the microorganism. Preferably, the glucose is linked after the separation. The method can be tailored toward detecting different types of microorganisms. Representative examples include bacteria (e.g., E. Coli.), bacterial toxins, and viruses (e.g., HIV, hepatitis).

In another embodiment, an enzyme tag is used instead of the glucose. The enzyme tag produces a color change when reacted, so that a calorimetric technique can be used to detect or measure the pathogen in the same way that colorimetric-based glucometer would be used with a glucose-induced color change.

In yet another embodiment, the glucose can be substituted with another sugar (e.g., mannose, fructose, galactose) that can be readily detected.

The magnetic separation step can be conducted using techniques known in the art, for example, as taught in U.S. Pat. No. 6,132,607, which is incorporated herein by reference. In one embodiment, a separation chamber is used which comprises a plurality of magnets and a plurality of channels having an inlet and an outlet. The magnets are arranged on one side of the channels and are in contact with one another to create a magnetic field. The magnetic particle containing-fluid is introduced into the inlet of the channels of the separation chamber, and the magnetic field of the magnets captures the microparticle-attached-components within the channels and the remaining mixture exits the outlet of the channels of the separation chamber.

Glucose concentration can be measured by any of a variety of known techniques. For example, the technique can be any one of three general methods: electrical, calorimetric, or acidity measurement. In a typical glucose testing system, the following glucose reaction is utilized:

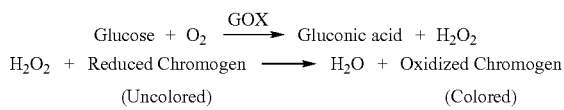

$$\text{Glucose} + O_2 \xrightarrow{\text{GOX}} \text{Gluconic acid} + H_2O_2$$
$$H_2O_2 + \text{Reduced Chromogen} \longrightarrow H_2O + \text{Oxidized Chromogen}$$
$$\text{(Uncolored)} \quad\quad\quad \text{(Colored)}$$

The colorimetric approach may be preferred. In a colorimetric assay, glucose is allowed to react with its enzyme, glucose oxidase (GOX), to form gluconic acid and hydrogen peroxide ($H_2O_2$). The hydrogen peroxide then is allowed to react with a reduced form of a chromogen compound to form a colored, oxidized chromogen compound, which can be monitored by reflectance photometry (Vote, et al., *Clinica Chimica Acta*, 305:81-87 (2001)). Glucose molecules, which are attached to the end of the conjugate, may be measured by multiple glucose measurement methods (electrical, colorimetric, and acidity measurement). Although the electrical method, which can be easily carried out by using a regular glucometer, is rapid, convenient and affordable, it may have in some embodiments a sensitivity problem that may need to be addressed, for example, by increasing the ability of the glucometer to detect small glucose concentrations. In one embodiment, the detection comprises measuring light transmittance through the test fluid. In another embodiment, the detection comprises measuring oxidation of the glucose to gluconic acid at a platinum electrode.

In one particular method, the presence or concentration of a bacterium in a fluid is detected. In one embodiment, the method includes combining the fluid with magnetic microparticles linked to a first biotinylated antibody, said first antibody binding to a first site on the bacterium, if any, present in the fluid; combining the fluid with a second biotinylated antibody, wherein the second antibody binds to a second site on the bacterium, wherein the second antibody is linked to a glucose molecule; using a magnetic field and a separation process to separate the linked bacterium from the fluid to form a test sample; and detecting the concentration of glucose in the test sample, wherein the glucose concentration correlates to the concentration of bacterium in the fluid sample. In a specific embodiment, the first biotinylated antibody comprises a biotinylated anti-*E. coli* Rabbit antibody, and the second biotinylated antibody comprises a biotinylated Con-A lectin linked to the glucose molecule. In one embodiment, the biotinylated Con-A lectin is linked to a streptavidin, and the streptavidin is linked to a biotinylated anti-*E. coli* endotoxin antibody.

In another aspect, a magnetic immunoassay system or kit is provided. In a preferred embodiment, the system includes . . .

The immunoassay can be provided in a kit form, similar to ELISA kits known in the art. In one example, the kit includes a first part which comprises magnetic microparticles bound to antibodies selected to be linkable to a first epitope of a microorganism of interest; and a second part which comprises a second antibody-streptavidin-lectin, wherein the lectin is selected to be linkable to glucose and the second antibody is selected to be linkable to a second epitope of the microorganism of interest.

In one form of the assays and methods described herein, the magnetic assay is a bacterial detection method that involves using streptavidin-biotin-antibody interaction. ELISA with SA-Biotin-Ab reaction is reported to have better assay sensitivity than the ELISA using the direct antibody absorption format (Hao et al., *Analytical Biochemistry*, 261(1):1-7 (1998)).

Accuracy of immunological methods is dependent upon the fidelity of the antibody-antigen binding. The literature indicates that the ability of monoclonal or polyclonal antibodies to bind *E. coli* cells, when present as pure cultures, is well documented (Shelton, et al., *J. Microbiological Methods* 55:717-25 (2003)). However, quantitative detection of *E. coli* in a sample requires that antibodies selectively bind to the bacterial cell wall. In Example 1 below, two categories of antibodies against *E. coli* were used, polyclonal and monoclonal. The polyclonal ones were not specific for only *E. coli* whereas monoclonal antibodies against *E. coli* Endotoxin were highly specific for only *E. coli*. However, the latter might react with all *E. coli* strains. Therefore, detecting a specific strain of *E. coli* would be expected to require a different specific set of antibodies to maintain test accuracy.

As used herein, the term "magnetic microparticles" includes magnetic, paramagnetic, superparamagnetic ferromagnetic and ferrimagnetic materials. The microparticles may comprise iron, nickel, cobalt, gadolinium, manganese and/or their alloys. In one embodiment, the microparticles comprise an iron oxide, such as magnetite, or more preferably, maghemite ($\lambda Fe_2O_3$). In other embodiments, the magnetic nanoparticles comprise an alloy or a mixture of elemental materials.

The microparticles preferably are in the form of microspheres, preferably less than 1 µm in diameter. In one preferred embodiment, the microspheres have a diameter of about 250 nm.

In a preferred embodiment, the microspheres have a magnetic core, preferably of a paramagnetic material, with a size of about 30 nm or less, which is encapsulated with a polymer or protein. Other core sizes may be acceptable, but desirably are of uniform size and less than 1 µm in diameter. In one embodiment, the magnetic particles comprise microspheres coated with albumin, avidin, or a combination thereof. In various embodiments, the magnetic particles may be encapsulated as described in U.S. Application Publication No. 2004/0065969 to Chatterjee, et al. and U.S. Application Publication No. 2004/0146529 to Chen, et al. The disclosures of these publications are expressly incorporated by reference herein.

Illustrative Embodiment

In one particular embodiment, a magnetic immunoassay has been developed for rapid detection of *Escherichia coli* BL21 Star (DE3) pLysS, a model pathogen. The magnetic immunoassay takes advantage of the multiple epitopes that are found on the target. A magnetic particle is attached on one epitope. On another epitope, a glucose molecule is attached. Glucometers known in the art have been designed with suitable accuracy to detect small amounts of glucose through the oxidation of glucose to gluconic acid at the site of a platinum electrode. The sandwich magnetic assay that contains the glucose label can be easily correlated to the concentration of the *Escherichia coli* BL21 Star (DE3) pLysS. In one embodiment, the detection technique that takes two hours to detect the exact amount of *E. coli* in the solution using a glucose detection technique.

In one embodiment, the sandwich immunoassay is formed by attaching two different antibodies to different epitopes on the same target antigen, e.g., the *E. coli* strain BL21 Star (DE3) pLysS. One antibody is attached to a solid surface of a magnetic or paramagnetic particle (e.g., a paramagnetic microsphere), and the other antibody is attached to a glucose molecule. The first antibody is used for the separation of the antigen (*E. coli*) from the sample, while the second antibody, attached to a glucose molecule(s), is used to measure the relative concentration of bacteria in the tested sample. Attaching glucose molecules at the end of the anti-bacterial endotoxin antibody facilitates the detection of the bacteria. For example, it can be readily measured using a conventional spectrophotometer at a wavelength of 500 nm. FIG. 1 shows a schematic representation of the magnetic immunoassay.

The technique, methods, and assays described herein for detecting *E. coli* strain BL21 Star (DE3) pLysS can be readily adapted for the detection of other bacterium or other microbial pathogens. For example, one can substitute the biotinylated antibodies for others specific to the microorganism of interest. The magnetic ELISA assay described herein can be applied or adapted to any sandwich immunoassay ELISA. It is predictable that this technique could be useful for the detection of a wide range of target antigens/pathogens, including HIV and hepatitis in blood, bacterial toxins (e.g. *Staphylococcus enterotoxins*), and bacteria (e.g. *Salmonella, listeria*), in various environments.

The use of a magnetic ELISA is described for quantitative detection of *E. coli* strain BL21 Star (DE3) pLysS. In one embodiment, the total time needed to complete the test is approximately 30-45 minutes. Assuming that both terminals of the conjugate are pre-prepared, the time needed is that needed to add the antigen (*E. coli*) to both conjugate's terminals and allow them to react. Overcoming the speed limitation that previous methods face is a major success and significant advantage of the methods described herein. The application of this assay will depend, however, on the user's particular requirements. The need for rapid results may or may not be balanced by other considerations.

The methods and compositions can be further understood with the following non-limiting examples.

EXAMPLE 1

Magnetic Immunoassay for *E. coli* BL21

Materials and Process

Magnetic microspheres (MMS) were produced using protocols that were established by Haik, et al., *J. Magnetism & Magnetic Materials* 194:254-61 (1999); Chatterjee, et al., *J. Magnetism & Magnetic Materials* 257:113-18 (2003). The MMS were coated with albumin and coupled with avidin to conjugate the anti-*E. coli* Rabbit antibody. Affinity purified antibodies, both rabbit antibody against *E. coli* and monotype antibody endotoxin against *E. coli* BL21, were obtained from ViroStat Company (Portland, Me., USA). The rabbit antibodies were already biotinylated, and the monotype antibodies endotoxin were biotinylated using an EZ-link Sulfo-NHS-LC biotinylation kit obtained from Pierce Chemicals (Rockford, Ill., USA). The antigen *E. coli* strain BL21 Star (DE3) pLysS was obtained from Invitrogen Corporation (Carlsbad, Calif., USA). Both Streptavidin (SA), isolated from the microorganism *Streptomyces avidinii*, and Concanavalin A (Con A) lectin were bought from Vector Laboratories (Burlingame, Calif., USA). Glucose oxidase reagent was obtained from TECO Diagnostics (Anaheim, Calif., USA).

The synthesis of the magnetic microspheres was accomplished according to the published protocol in three major steps (Chatterjee, et al., *J. Magnetism & Magnetic Materials* 257:113-18 (2003)): co-precipitation of ferrous chloride and ferric chloride by sodium hydroxide, material heating and sonication, and material peptization with nitric acid. Both ferrous and ferric chlorides were dissolved in a 1:2 molar ratio in distilled water. The solution then was mixed immediately with a highly concentrated sodium hydroxide, stirred continuously, heated to 90° C., and sonicated to produce ultra fine magnetic particles, which were finally peptized by nitric acid. Finally, the microspheres were coated with albumin and avidin to make them attachable to the biotinylated antibodies.

Two types of purified antibodies were used: monoclonal and polyclonal anti *E. coli* bacterial antibodies. The polyclonal type antibodies were prepared in rabbit against *E. coli* and were obtained conjugated with biotin molecules attached to the long arm of the antibodies. The other polyclonal type antibodies were specific to endotoxin receptors on *E. coli* bacterial cell wall, and they were biotinylated in the laboratory using an EZ-link Sulfo-NHS-LC biotinylation kit.

Endotoxin antibodies were biotinylated using an EZ-link Sulfo-NHS-LC biotinylation kit obtained from Pierce Chemicals. Long chain arm biotin containing a 22 Armstrong spacer arm between the reacted primary amine and the biotin moiety was used (see http://www.piercenet.com/files/0215dh4.pdf) to minimize the possible effects of steric hindrance when conjugating the biotin to the much larger MMS and to increase the sensitivity.

The amount of biotin molecules incorporated was determined using HABA method protocol. The total attached biotins to the endotoxin antibodies were 3.166 molecules per antibody. Biotinylated antibodies then were diluted in a ratio of 1:800 according to Chemicon International ELISA protocol and preserved refrigerated for further usage under −4° C.

Streptavidin (SA) was obtained from Vector Laboratories (Burlingame, Calif. USA). The SA is a 60,000 Dalton protein composed of four identical subunits; each one has a binding site for biotin. A concentration of (20 μL/ml) was prepared by mixing 50 μL in 2450 μL HEPES buffer solution (Suter, et al., *Molecular Immunology*; 26:221-30 (1989)).

The solution then was allowed to attach with Concanavalin-A lectin. The Con-A, which is one of the most widely used and well-characterized lectins, also was obtained from Vector Laboratories. It has broad applicability primarily because it recognizes a commonly occurring sugar structure, α-D-Mannose and α-D-Glucose through its four saccharide binding sites. At neutral and alkaline pH, Con-A exists as a tetramer of four identical subunits of approximately 26,000 Daltons each. Below pH 5.6, Con A dissociates into active dimers of 52,000 Daltons. Here, biotinylated Con-A lectins were prepared in a concentration of 1 μL/ml by mixing 2 μL Con-A with 9.998 μL HEPES buffer solution. The solution was kept refrigerated under −4° C. for further usage.

Decimal dilutions ($10^1$, $10^2$, $10^3$, $10^4$, $10^5$, and $10^6$) of *E. coli* BL21 were prepared in Trypticase soy broth and cultured in Trypticase soy agar and incubated overnight under 37° C. to count the growth of bacteria. Bacterial colonies were then counted. Each dilution was multiplied by its dilution factor and a final bacterial concentration of ($3.4 \times 10^9$ cell/ml) was calculated.

One milliliter of the prepared (1:800) ratio biotinylated anti-*E. coli* rabbit antibodies solution was combined with 7.6 ml of (0.01 g/ml) avidin coupled microsphere solution. These figures were obtained by using the HABA method to determine the minimum number of biotin groups on both antibody clones. Using the HABA method, a minimum of 15 biotin groups/antibody gave the 10 nmoles of avidin needed to couple with 0.1 mg of 908 antibodies. Each 0.076 g of avidin coupled microsphere solution has 10 nmoles avidin or 7.6 ml of solution at 0.01 g/ml. The final solution of antibodies and avidin-coupled microspheres were incubated while mixing at 30° C. for 30 minutes.

A further step was conducted to block any unreacted biotin molecules on rabbit antibodies or avidin molecules on the microspheres. This step was accomplished by adding human serum albumin (HSA) (0.05 mg/ml) solution to the preconjugated rabbit antibodies and microspheres and incubated at 30° C. for 30 minutes while mixing.

To reach the optimal performance between the reactants, a volume of 200 μl of biotinylated monotype antibody endotoxin for *E. coli* (1:800 ratio) was attached to the Con A-SA solution. Con-A and SA were prepared in the same concentrations described above, and a volume of 200 μl of each was added to attach each other in an eppendorf tube. The mixture was then incubated at 30° C. for 30 minutes while mixing.

All of the following reagents of (1 μg/ml) Con-A, (20 μg/ml) streptavidin, (1:800 Dilution) of each biotinylated antibodies, serial bacterial dilutions starting from ($1.7 \times 10^9$ to $0.0265 \times 10^9$), and (5 mg/ml) glucose solution were used to conduct the ELISA experiment.

The target conjugate of the experiment was composed of two major parts; each was prepared separately as follows. The first part (Endotoxin-SA-Con A) was formed by adding an exact volume amount of 200 μl of Con-A and SA together, and then allowing them to link together while shaking for 30 minutes at 30° C. Next, the same volume amount of biotinylated endotoxin antibodies was added to the mixture and allowed to react for 30 minutes at 30° C. while shaking.

The second part of the ELISA conjugate (rabbit antibody against *E. coli*-microspheres (MMS)) was formed by adding 600 μl of biotinylated Rabbit antibodies to 7.6 ml of (0.01 mg/ml) of MMS and incubated together for 30 minutes at 30° C. while shaking. Then, an addition of 1 ml of HSA was performed to block any unreacted active sites on the microspheres, to prevent any secondary signal that might result from the addition of the second part of the complex. Then, a 200 μl of each bacterial concentration was added to the conjugate and incubated under the same conditions.

To form the whole conjugate, the two major parts were combined and incubated for 30 minutes at 30° C. while shaking, and a 300 μl of glucose was added to each tube and incubated under the same incubation conditions. Next, two 1.5 Tesla magnets were applied to the side of each tube to isolate the reactants (SPM-Rabbit Antibody-*E. coli*-Endotoxin-SA-Con A-Glucose) from other excess solution.

The isolated reactants were then washed several times by Tris Buffered Saline (TBS) while the magnets remained applied. Then, a volume of 50 μl of each washed reactants was added to preheated tubes each contained 600 μl glucose oxidase enzyme reagent and read spectrophotometrically at 500 nm.

Results:

The determination of peripheral glucose molecules attached to the end of the whole conjugate was the key to indirectly determine the concentration of *E. coli* that was taken up by the conjugate. The preheated glucose oxidase enzyme reagent was incubated with a 50 μl samples for 10 min. in a water bath at 30° C. The chemical reaction that occurred between the glucose oxidase enzyme and its substrate (peripheral glucose) resulted in a pink-like color, which can be detected spectrophotometrically at $A_{500}$. Because the serial dilutions of *E. coli* were used and inserted in the conjugate, different color intensities resulted where each dilution correlated to the amount of *E. coli* that was linked on the conjugate.

Figure 2:
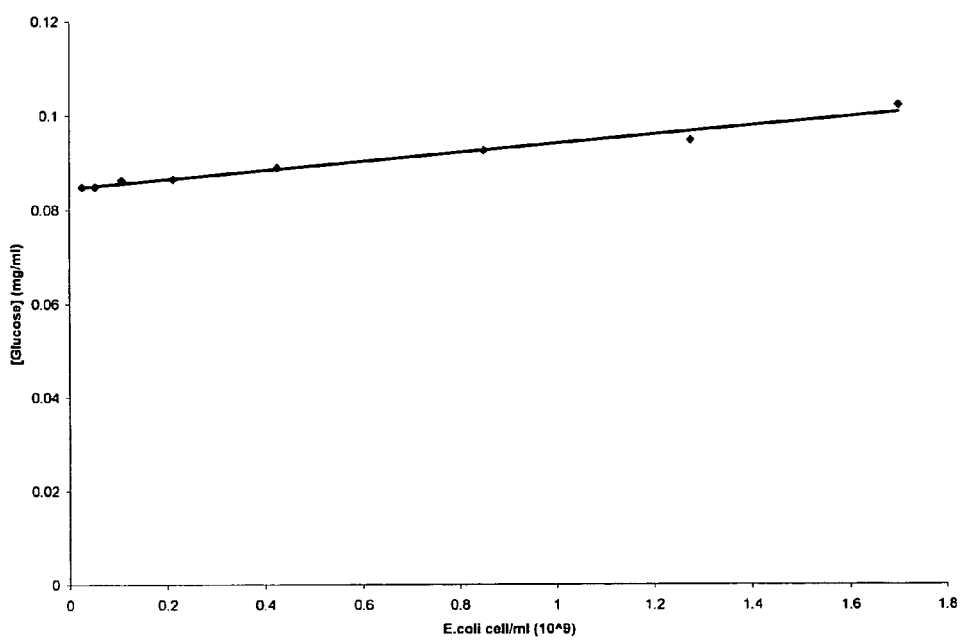
FIG. 2 is a graph showing the relationship between various concentrations of bacteria and their correlated glucose concentrations in one example.

FIG. 2 represents the relationship between various bacterial concentrations and their correlated glucose concentrations. The absorbencies of each bacterial dilution were matched with the standard absorbencies that were taken from the glucose standard curve, and the glucose concentration was calculated for each dilution using the curve standard equation $y = 41.046 x^{-0.1945}$.

Figure 3:
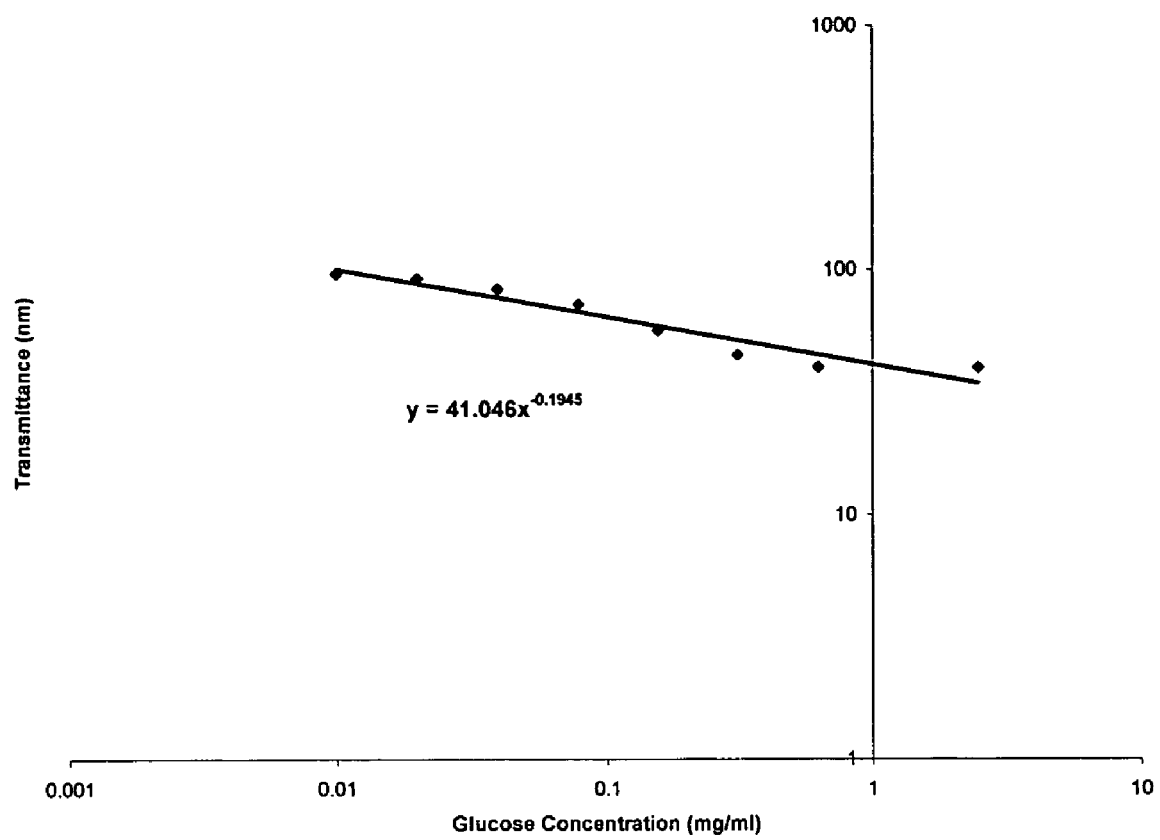
FIG. 3 is a graph showing the relationship between glucose concentration and transmittance in one example.

In order to standardize glucose measurements, serial glucose concentrations prepared in distilled water were treated under the same experimental conditions (preheated 600 μl glucose oxidase enzyme reagent and 50 μl glucose samples) and read spectrophotometrically at the same wavelength $A_{500}$. The resulting transmittances were different and logarithmically correlated with the various glucose concentrations. The highest concentration had the lowest transmittance, as shown in FIG. 3.

In one experiment, 600 μL of glucose oxidase reagent solution was warmed for 5 minutes in a water bath at 37° C., and then 50 μL of sample solution was added to the preheated reagent solution and incubated for 10 minutes in water bath under 37° C. The resulted solution had various intensities of pink color depicting the concentration of glucose in each sample.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. A method for detecting a target microorganism comprising:
   linking via a first antibody a magnetic microparticle to a first epitope of the target microorganism in a fluid;
   utilizing a magnetic field to separate the magnetic microparticle and linked targeted microorganism from at least a portion of other components in the fluid, thereby forming a test sample;
   linking via a second antibody a glucose molecule to a second epitope of the target microorganism; and
   detecting the glucose in the test sample to determine the presence or concentration, or both presence and concentration, of the target microorganism in the fluid.

2. The method of claim 1, wherein the target microorganism comprises a bacterium or bacterial toxin.

3. The method of claim 2, wherein the target microorganism comprises *E. Coli*.

4. The method of claim 1, wherein the target microorganism comprises a virus.

5. The method of claim 1, wherein the magnetic microparticles comprise microspheres coated with a polymer or protein.

6. The method of claim 5, wherein the coating comprises albumin, avidin, or a combination thereof.

7. The method of claim 1, wherein the glucose detection comprises measuring the electrical resistance, color, or pH of the test sample.

8. The method of claim 1, wherein the glucose detection comprise measuring light transmittance through the test sample.

9. The method of claim 1, wherein the glucose detection comprises oxidation of the glucose to gluconic acid at a platinum electrode.

10. The method of claim 1, wherein the fluid is obtained from blood or another mammalian physiological fluid.

11. The method of claim 1, wherein the first antibody comprises a biotinylated anti-*E. coli* rabbit antibody.

12. The method of claim 1, wherein the second antibody comprises an anti-*E. coli* endotoxin antibody.

13. The method of claim 1, wherein second antibody is linked to streptavidin.

14. The method of claim 13, wherein the streptavidin is linked to a lectin, which is linked to the glucose molecule.

15. A method for detecting a target bacterium in a fluid comprising:
   combining the fluid with magnetic microparticles linked to a first antibody, said first antibody binding to a first site on the target bacterium, if any, present in the fluid;
   applying a magnetic field to the fluid effective to separate the linked magnetic microparticles and target bacterium from the fluid, forming a test sample;
   combining the test sample with a second antibody, said second antibody binding to a second site on the target bacterium, wherein said second antibody is linked to a glucose molecule; and
   detecting the glucose in the test sample to determine the presence or concentration of the target bacterium in the fluid sample.

16. The method of claim 15, wherein the microparticles are microspheres which comprise a core of a superparamagnetic material coated with a protein or polymer.

17. The method of claim 15, wherein the first biotinylated antibody comprises a biotinylated anti-*E.coli* Rabbit antibody.

18. The method of claim 15, wherein the second biotinylated antibody is linked to streptavidin.

19. The method of claim 18, wherein the streptavidin is linked to a biotinylated lectin, which is linked to the glucose molecule.

20. The method of claim 19, wherein the biotinylated lectin is a Con-A lectin and the second biotinylated antibody comprises anti-*E.coli* endotoxin antibody.

* * * * *